United States Patent [19]

Vanden Heuvel

[11] 3,953,493

[45] Apr. 27, 1976

[54] SUBSTITUTED SULFONAMIDE DERIVATIVES AS ANTHELMINTIC AGENTS

[75] Inventor: William J. A. Vanden Heuvel, Princeton, N.J.

[73] Assignee: Merck & Co., Inc., Rahway, N.J.

[22] Filed: Mar. 27, 1975

[21] Appl. No.: 562,713

[52] U.S. Cl. .................... 260/465 E; 260/465 D; 260/556 AR; 260/556 B; 424/267; 424/321; 424/324

[51] Int. Cl.² .............................. C07C 143/80

[58] Field of Search...... 260/556 AR, 556 B, 465 E, 260/465 D; 71/103

[56] References Cited

UNITED STATES PATENTS

| | | | |
|---|---|---|---|
| 3,121,084 | 2/1964 | Winberg | 260/268 |
| 3,681,406 | 8/1972 | Beck | 71/103 X |
| 3,709,936 | 1/1973 | Fridinger et al. | 71/103 X |
| 3,772,277 | 11/1973 | Beck | 71/103 X |
| 3,821,276 | 6/1974 | Mrozik | 260/465 E |
| 3,824,233 | 7/1974 | Friedman | 260/465 E X |
| 3,828,079 | 8/1974 | Mrozik | 260/464 E X |
| 3,829,492 | 8/1974 | Miller et al. | 260/465 E X |
| 3,832,155 | 8/1974 | Beck | 71/103 |
| 3,880,644 | 4/1975 | Beck | 71/103 X |
| 3,888,897 | 6/1975 | Martin | 260/465 E |

FOREIGN PATENTS OR APPLICATIONS

| | | | |
|---|---|---|---|
| 900,111 | 7/1962 | United Kingdom | 260/556 AR |
| 1,251,147 | 10/1971 | United Kingdom | 260/556 AR |
| 45-15254 | 2/1967 | Japan | 260/556 AR |

Primary Examiner—Allen B. Curtis
Attorney, Agent, or Firm—J. Jerome Behan; David L. Rose

[57] ABSTRACT

Novel substituted benzenesulfonamides are disclosed in which the sulfonamide nitrogen is substituted with an N,N-dimethylaminomethylene group. The compounds are active anthelmintic agents and are particularly active against mature and immature fasciola. Processes for their preparation as well as compositions and methods for the treatment of helminthias are also disclosed.

6 Claims, No Drawings

SUBSTITUTED SULFONAMIDE DERIVATIVES AS ANTHELMINTIC AGENTS

SUMMARY OF THE INVENTION

This invention relates to novel sulfonamides and to methods for their preparation. In particular this invention relates to novel 3,4,5-substituted benzenesulfonamides in which the sulfonamido nitrogen is doubly bonded to an N,N-dimethylaminomethylene group. These novel compounds have antiparasitic and anthelmintic activity and are particulary active against liver fluke in sheep and cattle.

Thus, it is an object of this invention to provide for novel substituted benzenesulfonamides. It is a further object of this invention to provide for processes for the preparation of such compounds. Another object is to provide for compositions and methods for the treatment of parasitic diseases utilizing such compounds as the active ingredient. A still further object is to provide specifically for such compositions and method which are useful against fascioliasis or liver fluke infections in sheep and cattle.

DESCRIPTION OF THE INVENTION

The novel compounds of this invention are represented by the following structural formula:

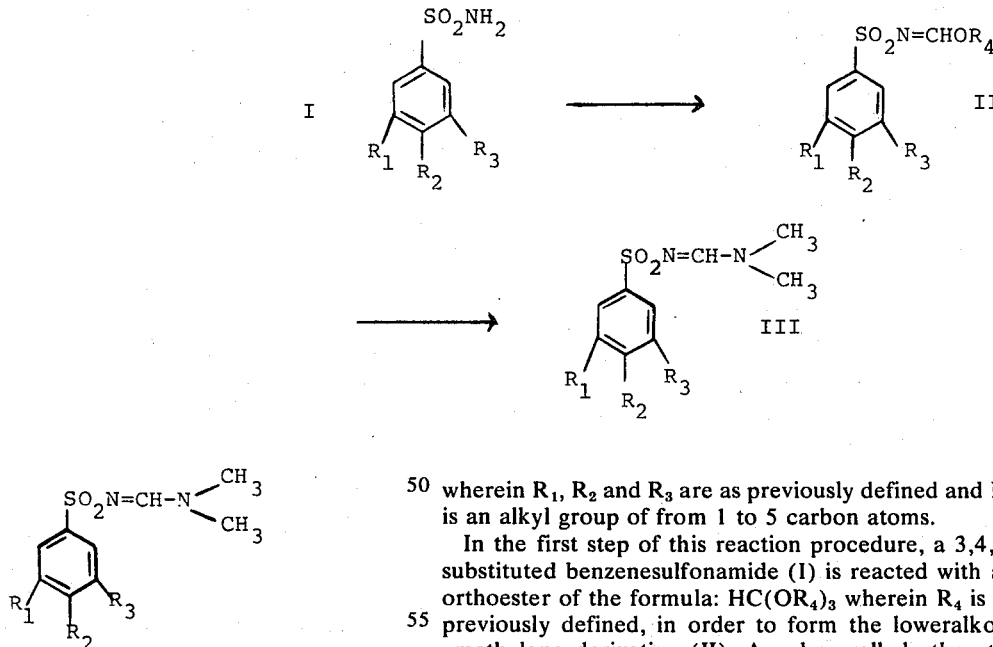

wherein
  $R_1$ is halo, nitro or trifluoromethyl;
  $R_2$ is hydrogen or amino; and
  $R_3$ is cyano or $R_1$.

As employed in the instant description, the term "halo" or "halogen" is defined as including the halogen atoms fluorine, chlorine, bromine or iodine.

Also included within the instant invention are the non-toxic pharmaceutically acceptable salts of the above compounds.

The novel compounds of this invention are useful as antiparasitic and anthelmintic agents. They are preferably employed in the treatment of fascioliasis in sheep and cattle and when so employed are combined with non-toxic carriers for either oral or parenteral use. The compositions in their various forms may contain from 0.01 to 95% of the active compounds and are administered to the animal infected with liver fluke at dosage levels of from 1 to 300 mg./kg. of animal body weight, preferably from 5 to 100 mg./kg. of body weight. The particular amount of active ingredient in a composition will depend upon the particular form of composition, whether it is a premix, finished medicated feed product, solid or liquid unit dosage form, parenteral unit dosage form and the like, and also the particular type of animal being treated, its age, weight, degree of infection and the like. These compositions and their method of use in treating liver fluke infections thus form other aspects of this invention.

The preferred compounds of this invention are exemplified, but not limited by the following list:

N,N-dimethyl-N'-(3,5-dibromophenylsulfonyl) formamidine

N,N-dimethyl-N'-(3-bromo-5-cyanophenylsulfonyl) formamidine

N,N-dimethyl-N'-(3-iodo-5-trifluoromethylphenylsulfonyl) formamidine

N,N-dimethyl-N'-(3-iodo-5-cyanophenylsulfonyl) formamidine

The compounds of the instant invention are prepared by processes which are best visualized in the following reaction scheme:

wherein $R_1$, $R_2$ and $R_3$ are as previously defined and $R_4$ is an alkyl group of from 1 to 5 carbon atoms.

In the first step of this reaction procedure, a 3,4,5-substituted benzenesulfonamide (I) is reacted with an orthoester of the formula: $HC(OR_4)_3$ wherein $R_4$ is as previously defined, in order to form the loweralkoxymethylene derivative (II). Any loweralkylorthoester may be employed, the product being dependent upon the particular ester employed. The reaction is generally run in an aprotic solvent such as chloroform, benzene, toluene, acetone, tetrahydrofuran and the like. The use of a solvent is, however, optional and the product may be obtained in equally good yields without any solvent. The reaction is run at from room temperature to the reflux temperature of the reaction medium and is complete in from 15 minutes to 6 hours. There is generally employed an excess of the orthoester over the sulfonamide although exactly one molar equivalent may be employed if desired. This intermediate product is recovered by techniques known to those skilled in this art.

The product compounds are prepared from the loweralkoxymethylene compounds (II) by treating the latter compound with dimethylamine in an optional aprotic solvent at from room temperature to the reflux temperature of the reaction mixture when a solvent is employed, and to 150°C when no solvent is employed. The reaction is generally complete in from ½ to 6 hours and the product is isolated by techniques known to those skilled in this art. One molar equivalent of dimethylamine is required for the completion of the reaction, however, generally an excess of dimethylamine, up to about 10 molar equivalents is generally employed.

The following Examples are typical of the procedures employed to synthesize the compounds of this invention. The Examples are presented so that the invention might be more fully understood and should not be construed as being limitative of the invention.

EXAMPLE 1

N,N-Dimethyl-N'-(3,5-dibromophenylsulfonyl) formamidine

371 Mg. (1 mmole) of O-ethyl-N-(3,5-dibromophenylsulfonyl) formimino ether is dissolved in 10 ml. of toluene at 35°C. Gaseous dimethylamine is bubbled through the solution for 5 minutes maintaining the temperature at 35°C. The reaction mixture is stirred overnight at room temperature whereupon some crystallization is observed. The reaction mixture is concentrated by heating in an oil bath at 170°C. Upon cooling to room temperature, the reaction mixture solidifies and is treated with ethyl acetate and filtered. The solid material is dried in vacuo at 50°C. affording 250 mg. of N,N-dimethyl-N'-(3,5-dibromophenylsulfonyl) formamidine, melting point 157° to 158°C. Recrystallization from dimethylsulfoxide/water gives pure N,N-dimethyl-N'-(3,5-dibromophenylsulfonyl) formamidine, melting point 160° to 162°C.

Following the procedure of Example 1 employing O-methyl-N(3,5-ditrifluoromethylphenylsulfonyl) formimino ether or O-butyl-N(3-chloro-5-trifluoromethyphenylsulfonyl) formimino ether in place of O-ethyl-N-(3,5-dibromophenylsulfonyl) formimino ether there is obtained N,N-dimethyl-N'-(3,5-ditrifluoromethylphenylsulfonyl) formamidine and N,N-dimethyl-N'-(3-chloro-5-trifluoromethylphenylsulfonyl) formamidine, respectively.

EXAMPLE 2

N,N-Dimethyl-N'-(3-cyano-5-iodophenylsulfonyl) formamidine

A solution of 364 mg. (1 mmole) of O-ethyl-N-(3-iodo-5-cyanophenylsulfonyl) formimino ether in 10 ml. of toluene at 35°C. is treated with diemthylamine gas until the solution is saturated. A precipitate forms and the mixture is stirred for one half hour at 35°C. and filtered. The solid material is washed with toluene and ether and dried affording 281 mg. (77%) of N,N-dimethyl-N'-(3-cyano-5-iodophenylsulfonyl) formamidine, melting point to 186° to 187°C.

Following the procedure of Example 2, employing O-butyl-N-(3-bromo-5-cyanophenylsulfonyl) formimino ether, O-ethyl-N-(3-cyano-5-trifluoromethylphenylsulfonyl) formimino ether or O-ethyl-N-(4-amino-3-bromo-5-cyanophenylsulfonyl) formimino ether in place of O-ethyl-N-(3-iodo-5-cyanophenylsulfonyl) formimino ether there is obtained N,N-dimethyl-N'-(3-bromo-5-cyanophenylsulfonyl) formamidine, N,N-dimethyl-N'-(3-cyano-5-trifluoromethylphenylsulfonyl) formamidine, and N,N-dimethyl-N'-(4-amino-3-bromo-5-cyanophenylsulfonyl) formamidine, respectively.

The starting materials for the above reactions are prepared in the following manner:

PREPARATION 1

O-Ethyl-N(3,5-dibromophenylsulfonyl) formimino ether

315 Mg. (1 mmole) of 3,5-dibromobenzenesulfonamide and 1.0 ml. of triethylorthoformate (3.75 mmoles) are combined and heated in an oil bath at 130°C. for 30 minutes. A clear solution is formed which stops bubbling after 20 minutes. The reaction mixture is cooled whereupon it solidifies completely. The solid material is washed with ethanol, centrifuged, washed again with ethanol and dried in vacuo at 50°C. recovering white crystals, melting point 137° to 139°C. 360 Mg. of O-ethyl-N(3,5-dibromophenylsulfonyl) formimino ether is recovered.

PREPARATION 2

O-Ethyl-N(3-iodo-5-cyanophenylsulfonyl) formimino ether 3.08 G. (10 mmoles) of 3-iodo-5-cyanobenzenesulfonamide and 10 ml. of triethylorthoformate are combined and heated in an oil bath at 130°C. with stirring. After 15 minutes a clear solution is formed and the reaction mixture starts to bubble which continues for 30 minutes. The reaction mixture is cooled to room temperature and allowed to stand for 1 hour. The reaction mixture is washed with ethanol, filtered, and washed again with ethanol affording a solid material melting at 138° to 140°C. 3.45 G. of a beige solid is recovered.

PREPARATION 3

O-Methyl-N(3,5-ditrifluoromethylphenylsulfonyl) formimino ether

293 Mg. (1 mmole) of 3,5-ditrifluoromethylbenzenesulfonamide and 1.0 ml. of trimethylorthoformate are combined and heated in an oil bath at 130°C. for 30 minutes. A clear solution is formed which bubbles for 20 minutes after reaching the reaction temperature. The reaction mixture is cooled whereupon it solidifies completely. The solid material is washed with methanol, centrifuged, washed again with methanol and dried in vacuo at 50°C. recovering white crystals of O-methyl-N(3,5-ditrifluoromethylphenylsulfonyl) formimino ether.

PREPARATION 4

O-Butyl-N(3-bromo-5-cyanophenylsulfonyl) formimino ether 2.61 G. (10 mmoles) of 3-bromo-5-cyanobenzenesulfonamide and 10 ml. of tributylorthoformate are combined and heated in an oil bath at 130°C. with stirring. After 15 minutes a clear solution is formed and the reaction mixture starts to bubble which continues for 30 minutes. The reaction mixture is cooled to room temperature and allowed to stand for 1 hour. The reaction mixture is filtered, and washed with butanol affording crystalline O-butyl-N-(3-bromo-5-cyanophenylsulfonyl) formimimino ether.

PREPARATION 5

O-Ethyl-N-(3-bromo-5-nitrophenylsulfonyl) formimino ether 2.81 G. (10 mmoles) of 3-bromo-5-nitrobenzenesulfonamide and 10 ml. of triethylorthoformate are combined and heated in an oil bath at 130°C. with stirring. After 15 minutes a clear solution is formed and the reaction mixture starts to bubble which continues for 30 minutes. The reaction mixture is cooled to room temperature and allowed to stand for 1 hour. It is filtered, and washed with ethanol affording crystalline O-ethyl-N-(3-bromo-5-nitrophenylsulfonyl) formimino ether.

What is claimed is:

1. A compound having the formula:

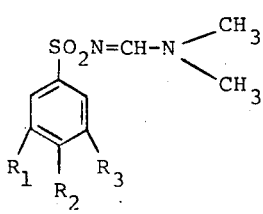

wherein
 $R_1$ is halo, nitro or trifluoromethyl;
 $R_2$ is hydrogen or amino; and
 $R_3$ is cyano or $R_1$.

2. The compound of claim 1 which is N,N-dimethyl-N'-(3,5-dibromophenylsulfonyl)-formamidine.

3. The compound of claim 1 which is N,N-dimethyl-N'-(3-bromo-5-cyanophenylsulfonyl)-formamidine.

4. The compound of claim 1 which is N,N-dimethyl-N'-(3-iodo-5-trifluoromethylphenylsulfonyl)-formamide.

5. The compound of claim 1 which is N,N-dimethyl-N'-(3-iodo-5-cyanophenylsulfonyl)-formamidine.

6. A process for the preparation of a compound having the formula:

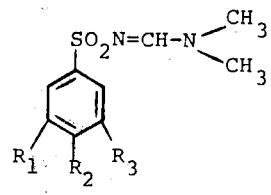

wherein
 $R_1$ is halo, nitro or trifluoromethyl;
 $R_2$ is hydrogen or amino; and
 $R_3$ is cyano or $R_1$;
which comprises treating a compound having the formula:

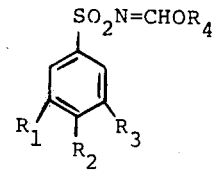

wherein $R_1$, $R_2$ and $R_3$ are as previously defined and $R_4$ is an alkyl group of from 1 to 6 carbon atoms, with dimethylamine.

* * * * *